United States Patent
Robinson et al.

(10) Patent No.: US 10,479,906 B2
(45) Date of Patent: Nov. 19, 2019

(54) USE OF FUNGAL PIGMENTS FROM WOOD-STAINING FUNGI AS COLORANTS IN WOOD FINISHES AND PAINTS

(71) Applicant: Oregon State University, Corvallis, OR (US)

(72) Inventors: Sara C. Robinson, Corvallis, OR (US); Sarath Mercedes Vega Gutierrez, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/266,865

(22) Filed: Sep. 15, 2016

(65) Prior Publication Data
US 2017/0081540 A1 Mar. 23, 2017

Related U.S. Application Data

(60) Provisional application No. 62/220,694, filed on Sep. 18, 2015.

(51) Int. Cl.
| | | |
|---|---|---|
| C09D 17/00 | (2006.01) | |
| C09D 15/00 | (2006.01) | |
| C09D 133/10 | (2006.01) | |
| C12P 1/02 | (2006.01) | |

(52) U.S. Cl.
CPC .......... C09D 17/003 (2013.01); C09D 15/00 (2013.01); C09D 17/002 (2013.01); C09D 133/10 (2013.01); C12P 1/02 (2013.01)

(58) Field of Classification Search
CPC ..... C09D 17/003; C09D 17/005; C09D 15/00
See application file for complete search history.

(56) References Cited

U.S. PATENT DOCUMENTS

| | | | | |
|---|---|---|---|---|
| 3,906,112 A * | 9/1975 | Anderson | ............. | C07C 403/24 426/1 |
| 4,851,339 A * | 7/1989 | Hills | ............. | C07C 403/24 435/67 |
| 4,919,721 A * | 4/1990 | Hermann | ............. | C09D 191/005 106/227 |
| 5,318,902 A * | 6/1994 | St. Martin | ............. | C09B 61/00 435/117 |
| 5,830,738 A * | 11/1998 | Thomas | ............. | C07C 403/24 435/209 |
| 6,261,622 B1 * | 7/2001 | Koguchi | ............. | A23L 2/58 426/540 |
| 6,827,941 B1 * | 12/2004 | Luddecke | ............. | A23L 2/58 424/401 |
| 2001/0008644 A1 * | 7/2001 | Stein | ............. | C07C 403/24 426/73 |
| 2002/0082459 A1 * | 6/2002 | Bailey | ............. | C07C 403/24 585/351 |
| 2004/0150702 A1 * | 8/2004 | Tsuyoshi | ............. | C09D 11/322 347/100 |
| 2008/0193539 A1 * | 8/2008 | Voelker | ............. | A61Q 19/00 424/488 |
| 2011/0088590 A1 * | 4/2011 | Ahlnas | ............. | A01N 37/02 106/18.31 |
| 2013/0115345 A1 * | 5/2013 | Miuchi | ............. | A23L 2/52 426/268 |
| 2013/0302365 A1 * | 11/2013 | Weber | ............. | A23L 1/2755 424/195.17 |
| 2016/0157477 A1 * | 6/2016 | Ballinger, Jr. | ........ | A01M 29/08 119/713 |

FOREIGN PATENT DOCUMENTS

WO WO 2012/119228 9/2012

OTHER PUBLICATIONS

Robinson et al., "Feasibility of using red pigment producing fungi to stain wood for decorative applications," *Can. J. For. Res.*, vol. 41, pp. 1722-1728, Aug. 10, 2011.

Robinson et al., "Utilizing Extracted Fungal Pigments for Wood Spalting: A Comparison of Inducted Fungal Pigmentation to Fungal Dyeing," *Journal of Coatings*, vol. 2014, 9 pages, Oct. 7, 2014.

Robinson et al., "Wood Colorization through Pressure Treating: The Potential of Extracted Colorants from Spalting Fungi as a Replacement for Woodworkers' Aniline Dyes," *Materials*, vol. 7, pp. 5427-5437, Jul. 24, 2014.

Venil et al., "Bacterial pigments and their applications," *Process Biochemistry*, vol. 48, pp. 1065-1079, Jun. 10, 2013.

Weber et al., "Pigments extracted from the wood-staining fungi *Chlorociboria aeruginosa, Scytalidium cuboideum*, and *S. ganodermophthorum* show potential for use as textile dyes," *Coloration Technology*, vol. 130, pp. 445-452, Aug. 22, 2014.

\* cited by examiner

*Primary Examiner* — Liam J Heincer
(74) *Attorney, Agent, or Firm* — Klarquist Sparkman, LLP

(57) ABSTRACT

Compositions containing fungal pigments and methods for making the compositions are described, as are methods of staining, painting or dyeing objects with such compositions.

28 Claims, No Drawings

USE OF FUNGAL PIGMENTS FROM WOOD-STAINING FUNGI AS COLORANTS IN WOOD FINISHES AND PAINTS

This application claims the benefit of U.S. Provisional Application No. 62/220,694, filed Sep. 18, 2015, which is incorporated by reference herein.

BACKGROUND

There is a long history of use of natural and synthetic colorants on wood products to enhance visual appeal. Two primary forms of colorants are utilized by modern woodworkers—modern "ease of use" aniline dyes, referring to powdered synthetic dyes that can be solubilized in alcohol or hydrated in water, and spalted wood, referring to wood that has been given color(s) through colonization of a very select group of fungi. However, the past two decades have seen a growing interest in switching from modern aniline dye methods for coloring wood to the use of entirely spalted wood. This shift has presented numerous problems for the woodworking community, as aniline dyes can be cheaply purchased and readily applied to finished or unfinished wood products with little effort. Spalted wood, on the other hand, must either be found in nature before the decay effects of the fungi have been fully realized, thus rendering the wood unusable, or the spalting must be induced in clear wood—a process that can take months to several years with unreliable results.

SUMMARY

Disclosed herein is a composition comprising a fungal pigment suspended or solvated in an oil carrier.

Also disclosed herein is a composition comprising a fungal pigment suspended or solvated in wood stabilizing (meth)acrylic resin.

Disclosed herein is a composition comprising a fungal pigment suspended or solvated in an acrylic resin.

Further disclosed herein is a method for staining or dyeing an object, comprising applying to the object the compositions disclosed herein.

Additionally disclosed herein is a method for painting an object, comprising applying to the object the compositions disclosed herein.

Also disclosed herein is a method for making a composition comprising:

preparing a fungal pigment/organic solvent solution or suspension;

mixing the fungal pigment/organic solvent solution or suspension with an oil carrier; and evaporating the organic solvent resulting in a composition comprising the fungal pigment suspended or solvated in the oil carrier.

Still further disclosed herein is a method for extracting a fungal pigment from an object comprising applying to the object a composition comprising a fungal pigment suspended or solvated in an oil carrier.

Also disclosed herein is a method for resolubilizing a fungal pigment comprising contacting a fungal pigment with the compositions disclosed herein to provide a composition comprising the fungal pigment suspended or solvated in an oil carrier.

Additionally disclosed herein is a method for making a composition comprising:

preparing a fungal pigment/organic solvent solution or suspension;

mixing the fungal pigment/organic solvent solution or suspension with a water carrier; and removing the organic solvent resulting in a composition comprising the fungal pigment suspended or solvated in the water carrier.

Also disclosed herein is a method for growing a fungal pigment culture in an aqueous media growth suspension while continuously agitating the suspension.

The foregoing will become more apparent from the following detailed description.

DETAILED DESCRIPTION

Fungi produce a wide variety of pigments. Wood-inhabiting fungi that secrete penetrating extracellular pigment are relatively rare. Their pigments are thought to be secreted as a form of resource capture whereby the pigments are naturally anti-fungal, and being in the wood substrate keeps other fungi from colonizing. Because of this, these pigments tend to be UV stable and not readily able to be removed from wood by water. Extracellular pigments that are produced by wood staining fungi, specifically those fungi which create pigment deeply inside wood, have unique chemical properties that allow them to adhere to various substrates in a permanent manner.

The natural aqueous insolubility of the fungal pigments, combined with their inherent 'stickiness' (binding ability), makes them potentially ideal dyes. However, these characteristics also mean that they have not been well studied or utilized as dyes because of the difficulty of working with them. Removing them from wood requires volatile organic solvents (VOCs) like dichloromethane (DCM), chloroform, and pyridine. They can be removed to a lesser extent by acetone, tetrahydrofuran, and acetonitrile, although the carrying capacity of these latter solvents is low and thus they are not good carriers. DCM, chloroform, and pyridine are toxic solvents with environmental concerns as well. Hence, if the pigments need to be carried in these solvents, they will not be significantly commercially utilized.

When a VOC solvent evaporates, the fungal pigment sticks to the nearest surface (like glass), and does not stay in suspension. It has been surprisingly discovered that oils can function as very effective liquid carriers for fungal pigments. The oil carrier provides several advantages over an organic solvent carrier. The fungal pigment/oil system disclosed herein provides a biological pigment for wood finishes that spreads evenly and is actually meant to be in wood. The fungal pigment/oil system disclosed herein solves the problem of how to carry the fungal pigments without solvents.

If the fungal pigment in an organic solvent carrier suspension is added to a paint (including both water-based acrylics and oil-based paints), the solvent degrades the paint and the fungal pigment would not remain in the paint once the solvent evaporated and would either stick to the glass container, or react with the paint, change color, and separate. However, when the fungal pigment is bound in an oil or water carrier (depending on whether an oil or acrylic paint is used, respectively), as disclosed herein, the fungal pigments blend with the paint and do not drop out or react. The oil and water may separate from the paint, but mix back together easily with simple stirring. Oil or water can be an ideal carrier for these pigments.

Further problematic issues arise with organic solvent carriers—due to polarity issues and the nature of the solvents, treating textiles, wood, etc with the pigments in solvents means that the pigments do not bind unless the solvent evaporates—the pigment prefers the polarity of the solvent to the polarity of the object they are supposed to dye. Once the organic solvent evaporates, the pigment binds to the substrate. As evaporation only happens from surfaces, no internal coloring occurs. When less-suitable organic solvents are used (lower carrying capacity, but less polarity so the pigment may bind to the substrate while still in suspension) the pigment is so perfectly dispersed that the effect is similar to a dot-matrix printer. The pigment is laid down in tiny dots and no overall color change can be seen. Oil and water seem to carry the pigment 'less well' as compared to an organic solvent, in that the pigment is either not perfectly dispersed, or dispersed only with continuous shaking. This leaves an actual visual color change that penetrates objects that are colored with the oil-based system disclosed herein.

The fungal pigment/oil systems/water systems disclosed herein are aptly suited for colorants in wood finishes of all types as they can be carried in various oils or water, which optionally may be mixed into oil or water-based finishes as suitable as a suspension or solution and, once on the wood, react as they would if dispersed by the fungus. This gives the wood a spalted look while also carrying a protective finish.

Illustrative oils that could be used as carriers include plant oils, mineral oils, and animal oils. Preferred oils include vegetable oils such as, for example, sunflower, olive (extra virgin, light, etc), walnut, tung, linseed (e.g., refined, sun thickened or cold pressed), Danish oil, or a mixture thereof. Another carrier is Cactus Juice wood stabilizing (meth) acrylic resin. As used herein, the designation "(meth) acrylic" and similar designations are used as abbreviated notation for acrylic, methacrylic, or mixtures thereof.

Illustrative fungal pigments include those extracted from, for example, fungi in the *Chlorociboria* genus, especially *C. aeruginascens* and *C. aeruginosa*, fungi in the *Scytalidium* genus, especially *S. cuboideum, S. lignicola* and *S. ganodermophthorum, Inonotus hispidus*, fungi in the *Monascus* genus, fungi in the order Helotiales, fungi in the subdivision Pezizomycotina, *Auricularia polytricha, Nectriaceae* genus, *Xylogone* genus, *Chlonostachis* genus, *Nectria* genus, especially *Nectria marinaeae, Peniophora* genus, *Trichoderma* genus, *Pestalotiopsis* genus, *Cosmospora* genus, *Bionectria* genus, *Cerioporiopsis* genus, or a mixture thereof.

The fungal pigment(s) may be mixed with the oil carrier(s) utilizing any method that provides a suspension or solution of the pigment in the oil carrier medium. In a certain embodiment, the pigment is initially suspended or solvated in an organic solvent (e.g., a VOC such as DCM) and the pigment/organic solvent solution or suspension is mixed into an oil carrier. The organic solvent is then evaporated off leaving the pigment solvated or suspended in the oil carrier. According to a particular example, the pigments suspended or solvated in DCM are poured into a given volume of an oil carrier and stirred, with a lid on to prevent DCM evaporation, for five minutes. After this, the DCM solvent is evaporated off (using a rotovap to prevent greenhouse gas emission and to recover all DCM), leaving the pigment in the oil solution.

The water-based pigments may be generated utilizing any method that provides a suspension or solution of the pigment in the water carrier medium. In a certain embodiment, the pigment can be generated by growing the fungal cultures in a 2% malt water suspension, which may be continuously rotated or shaken. In other embodiments, any suitable sugar source may be used to grow the fungal culture, such as potato dextrose or any other grains or starches that contain glucose, maltose, and/or maltotriose, or any mixtures thereof, in concentrations ranging from about 1% to about 5%. This solution of water-solubilized pigments may be mixed with water-based acrylic paints and/or finishes directly. In an embodiment, the addition is done within one day from when the shake culture is removed from the rotation or shaker table.

The fungal pigment(s) may be used to directly resolubilize a dry pigment from a substrate such as glass by adding an oil and, for example, allowing it to sit in a container with the substrate long enough to pick up the pigment, or by rotating or shaking the container to promote a speedier solubilization. Oil may be used to directly extract the pigment from wood substrates (including naturally found and artificially made pigments in a lab) by grinding the wood into a powder and mixing the powder with the oil. The resulting solution or suspension may be filtered to remove particulates, to provide a pigmented oil solution. In an embodiment, the resulting suspension is not filtered, to provide a pigmented oil suspension. An oil may also be used to directly extract from water-carried pigments as described above, such as by mixing an oil with the water solution and then separating the pigmented oil, for example via a separatory funnel or other similar separation mechanism.

The amount of fungal pigment suspended or solvated in the oil or water carrier may vary. All carriers for the pigment have a given carrying capacity. Once this capacity has been reached, the pigment may begin to bind to a glass container, bind to itself (i.e. forming a suspension instead of a solution), or the solution begins to separate and form layers. An ideal carrier solution is one where the color is maximized without the pigment dropping out of solution.

The fungal pigmented/oil systems/water systems disclosed herein may be used, for example, in wood finishes (both oil and water-borne) for flooring, for outdoor use (for example, for decking or outdoor furniture), woodcraft, furniture, and wood turning, and in artists' and commercial house paints (both oil paints and acrylic paints). The fungal pigmented/oil systems/water systems disclosed herein may also be used as general colorants across a broad spectrum of applications, including textile dyes, stone, and glass.

In certain embodiments, the pigments may be extracted from the fungi via techniques described in Robinson, S. C., Weber, G., Hinsch, E., Vega Gutierrez, S., Pittis, L., Freitas, S. 2014. Utilizing extracted fungal pigments for wood spalting—a comparison of induced fungal pigmentation to fungal dyeing. Journal of Coatings, article ID 759073, doi: 10.1155/2014/759073; and Weber, G., Chen, H-L., Hinsch, E., Freitas, S., Robinson, S. C. 2014. Pigments extracted from the wood-staining fungi *Chlorociboria aeruginosa, Scytalidium cuboideum*, and *S. ganodermophthorum* show potential for use as textile dyes. Coloration Technology 130(6):445-452.

EXAMPLES

Pigments are xylindein from *Chlorociboria* spp. (blue-green), red pigment from *Scytalidium cuboideum*, and yellow pigment from *S. ganodermophthorum*. Oils Tested: walnut oil, refined linseed oil, tung oil, sun thickened linseed oil, cold pressed linseed oil, danish oil, 'Cactus Juice' (a wood stabilizer used for spalted wood, made of mixed (meth)acrylate esters; listed as "hardener" below), and raw linseed oil.

Below are the percentages of pigment each oil can hold in complete suspension (i.e. its carrying capacity). The amount of pigment was calculated on suspension volume in DCM at a standard color reading (the standard color reading process is described in the references by Robinson, et al, and Weber, et al, listed above).

Green
walnut: did not carry
refined: 220%
tung: 140%
sun: 140%
cold: 180%
danish: 280%
hardener: 380%
Red
walnut: 740%
refined: 180%
tung: 180%
sun: 180%
cold: 200%
danish: 540%
hardener: 720%
Yellow
walnut: 860%
refined: 220%
tung: did not carry
sun: 140%
cold: 160%
danish: 640%
hardener: 720%
For the holding capacities of the oils: raw linseed oil holds red at 1200%, blue at 800%, and yellow at 1000%.
Results from pressure treating. The hardener penetrates spalted wood (maple) and leaves the pigment in the white rot areas, resulting in dyed, hardened wood. The oil pigments mix well with many paints.

Methodology

Pigments. Extracellular pigments were collected from *Scytalidium cuboideum* (pink/red-UAMH 4802, isolated from oak, location unknown), *Scytalidium ganodermophthorum* (yellow-UAMH 10320 from South Korea), and *Chlorociboria aeruginosa* (blue/green-UAMH 11657, isolated from a hardwood log in Ontario, Canada) following the protocol established in Robinson, S. C., Hinsch, E., Weber, G., Freitas, S. 2014; Method of extraction and resolubilization of pigments from *Chlorociboria aeruginosa* and *Scytalidium cuboideum*, two prolific spalting fungi; Coloration Technology 103:221-225. Fungi were grown on 2% malt agar plates amended with white rotted sugar maple chips and then the plates were shredded, placed in dichloromethane (DCM), and the pigment extracted.

Pigments were standardized to 100% concentration using the baseline established in Hinsch, E., Weber, G., Chen, H-L, Robinson, S. C. 2015; Colorfastness of extracted wood-staining fungal pigments on fabrics—a new potential for textile dyes; Journal of Textile Apparel, Technology and Management 9(3):1-11, where concentration is determined by color, not by weight of pigment: *C. aeruginosa*: $L^*=82.28$, $a^*=-11.06$, $b^*=-5.40$; *S. cuboideum*: $L^*=82.32$, $a^*=26.84$, $b^*=13.19$; *S. ganodermophthorum*: $L^*=95.46$, $a^*=-3.00$, $b^*=-8.15$. All pigments were stored suspended in DCM until use.

Submersion in oils. Seven oils were chosen for testing based upon ease of availability and prevalence of use in wood coatings and/or other artistic applications: refined linseed oil (Gamblin Artist's Colors), tung oil (Wood River), sun-thickened linseed oil (Grumbacher), cold-pressed linseed oil (Gamblin Artist's Oil Colors), Danish oil (Tried & True), walnut oil (Dr. Adorable Inc.), and raw linseed oil (Sunnyside). The carrying capacity for each oil was tested with each pigment, with carrying capacity defined as the maximum amount of pigment held in solution after evaporation of DCM, without the pigment clumping or binding.

Carrying capacity was determined by placing one mL by volume of oil in a 20 mL wide mouth glass scintillation vial (VWR International), then adding one mL by volume of a pigment in DCM. The DCM was then evaporated off and the solution left to sit overnight. In the morning the solution was inspected for complete solubilization. If pigment bound to the glass, had fallen to the bottom, or otherwise clumped together, carrying capacity was exceeded. Any oil that could not carry at least the same volume of pigment (1:1 ratio) was considered a failure, and not used for further testing. When carrying capacity was reached, the testing was refined to half mL and one quarter mL by volume to more accurately define the exact capacity of each oil.

Tests. Color change from the base oil color was done through liquid color reading using a Konica Minolta CR-5 colorimeter. Solid colors (red/pink, yellow, blue/green) were read at carrying capacity, one-half carrying capacity, and two-thirds carrying capacity. In addition, pigments suspended in oil were mixed together in scintillation vials to determine if the colors were additive. Oil pigments were mixed at following rations: 1:1, 2:1, 3:1, 4:1, 1:2, 1:3, and 1:4. The blue-green, red, and yellow mixture was only performed at a 1:1:1. A minimum of three replicates were used for each combination. Color change calculations were done using delta E. For solid colors, the base color used was the original color of each respective oil. For mixtures, three different calculations were run: delta E with original oil color as base, delta E with carrying capacity of pigment A in respective oil as base, and delta E with carrying capacity of pigment B in respective oil as base.

Analysis. Data were separated by color (blue, yellow, red, blue-red, blue-red-yellow, blue-yellow, red-yellow). Two-way ANOVAs were run with oil type and distribution as the independent variables, and color change (delta E) as the dependent variable. ANOVAs were followed by Tukey HSD to determine where differences lay. As only one distribution level (1:1:1) was used for the triple blend of the colors, a one-way ANOVA was used for this test.

For dilution tests, delta E was calculated using the base oil color only as the control. All blend data were run using three different delta E numbers (in the case of the blue/red/yellow blend, there were four delta E calculations). The first delta E was calculated using the base oil as the control (linseed, Danish, etc.). The second delta E was calculated with control readings from the first pigment of interest (carrying capacity of pigment 1 in the oil of interest), and the third delta E was calculated with control readings from the second pigment of interest. Changing the control in the delta E calculation allowed for elucidating whether the final delta E value varied from a specific color, instead of just an overall vary from the base oil.

Results

Carrying capacity. The blue/green pigment did not carry in walnut oil. Carrying capacity was reached at the following points for the oils: refined linseed oil-220%, tung oil-140%, sun-thickened linseed oil-140%, cold-pressed linseed oil-180%, Danish oil-380%, raw linseed oil-800%.

The red/pink pigment carried in all oils. Carrying capacity was reached at the following points: walnut oil-740%, refined linseed oil-180%, tung oil-180%, sun-thickened linseed oil-180%, cold-pressed linseed oil-200%, Danish oil-540%, raw linseed oil-1200%.

The yellow pigment did not carry in tung oil. Carrying capacity was reached at the following points: walnut-860%, refined linseed oil-220%, sun-thickened linseed oil-140%, cold-pressed linseed oil-160%, Danish oil-640%, raw linseed oil-1000%.

Dilutions. For solid blue/green, no dilutions had a higher delta E value than the full concentrations. The two-way ANOVA was significant at P<0.0001. The most color change came from the full concentration of cold-pressed oil (28.77) and the full concentration of linseed oil (26.469). However the delta E values for these oils were not significantly different from the Danish oil 2/3 dilution (25.419) or the cold-pressed ⅔ dilution (21.70). There was no significant color change for any of the dilutions done with sun-thickened linseed oil, tung oil, or refined linseed oil. For cold-pressed linseed oil, the color of the full concentration and two-thirds dilution did not differ, but the half concentration was significantly less. For raw linseed oil the highest delta E was with the full concentration, but the two-thirds and one-half dilutions did not differ from one another. For Danish oil, the full and two-thirds concentration did not differ significantly, but the one-half dilution had significantly lower delta E values.

For solid red/pink, the two-way ANOVA was significant at P<0.0001. Danish oil at full concentration had the highest delta E value (36.55), but was not significantly different from many others (see Table 1). There was no difference between the full concentrations and dilutions for cold-pressed linseed oil, refined linseed oil, and tung oil. Full concentrations had significantly higher delta E values than the dilutions for raw linseed and sun-thickened linseed oil. Danish oil had no difference between the full concentration and the two-thirds dilution, but both had a higher delta E value than the one-half dilution. Walnut oil's delta E did not differ significantly between full and two-thirds, nor two-thirds and one-half, but did differ between the two groups.

TABLE 1

Delta E values and significant differences for solid red/pink pigment in oils: CP = cold-pressed oil, D = Danish oil, L = raw linseed oil, R = refined linseed oil, ST = sun-thickened linseed oil, T = tung oil, W = walnut oil. Different letters indicate significant differences at alpha = 0.05.

| Oil | Dilution | N | Mean | SD | Significant Difference |
|---|---|---|---|---|---|
| CP | full | 5 | 30.07 | 1.78 | ABCD |
| CP | half | 3 | 27.71 | 0.55 | BCDEF |
| CP | two-thirds | 3 | 25.4 | 0.16 | CDEFG |
| D | full | 5 | 36.55 | 0.27 | A |
| D | half | 3 | 25.67 | 0.13 | CDEFG |
| D | two-thirds | 3 | 29.4 | 0.36 | ABCDE |
| L | full | 5 | 32.13 | 1.11 | ABC |
| L | half | 3 | 18.64 | 0 | G |
| L | two-thirds | 3 | 18.74 | 0.09 | G |
| R | full | 5 | 30.59 | 4.45 | ABCD |
| R | half | 3 | 30.81 | 0.13 | ABCD |
| R | two-thirds | 3 | 30.23 | 0.44 | ABCD |
| ST | full | 5 | 33.8 | 0.51 | AB |
| ST | half | 3 | 24.76 | 0.29 | DEFG |
| ST | two-thirds | 3 | 22.05 | 5.21 | FG |
| T | full | 5 | 26.4 | 3.83 | CDEF |
| T | half | 5 | 24.7 | 1.06 | DEFG |
| T | two-thirds | 3 | 21.96 | 3.7 | FG |
| W | full | 5 | 27.68 | 5.99 | BCDEF |
| W | half | 3 | 32.31 | 0.85 | ABC |
| W | two-thirds | 3 | 22.45 | 1.39 | EFG |

For solid yellow, the two-way ANOVA was significant at P<0.0001. The highest delta E came from raw linseed oil at full concentration (37.03), but it did not significantly differ from Danish oil at two-thirds concentration (30.07). There were no significant differences between any concentration for cold-pressed linseed oil, refined linseed oil, sun-thickened linseed oil, and walnut oil. Danish oil had a higher delta E value for the two-thirds dilution than the full or the one-half dilution, and the full and one-half dilution did not differ from each other. Raw linseed oil had a higher delta E value for the full concentration, and the two-thirds and one-half did not differ from one another.

Blends.

Blue red blend. When using a delta E with a base oil control, the two-way ANOVA was significant at P<0.0001. The most color change came from cold-pressed oil with a ratio of one blue-green to two red (39.59), however the amount of color change was not significantly different from many others (see Table 2), including any of the other cold-pressed concentrations. Likewise, Danish, raw linseed, and sun-thickened oil blends did not differ significantly from one another in terms of color change. Refined linseed oil had significantly more color change from the base oil control as the amount of red pigment increased. Tung oil showed more color change as the green pigment increased.

TABLE 2

Delta E values and significant differences for blends of blue-green and red pigments in oils. Control values use base oil color. CP = cold-pressed oil, D = Danish oil, L = raw linseed oil, R = refined linseed oil, ST = sun-thickened linseed oil, T = tung oil, W = walnut oil. Different letters indicate significant differences at alpha = 0.05.

| Oil | Distribution | N | Mean | SD | Significant Difference |
|---|---|---|---|---|---|
| CP | 1 to 1 | 3 | 35.1 | 4.73 | ABC |
| CP | 1 to 2 | 3 | 39.59 | 80.06 | A |
| CP | 1 to 3 | 3 | 31.72 | 1.99 | ABCDE |
| CP | 1 to 4 | 3 | 31.48 | 1.06 | ABCDE |
| CP | 2 to 1 | 3 | 37.96 | 7.54 | AB |
| CP | 3 to 1 | 3 | 34.18 | 5.45 | ABC |
| CP | 4 to 1 | 3 | 33.54 | 5.44 | ABC |
| D | 1 to 1 | 3 | 29 | 2.75 | ABCDEFG |
| D | 1 to 2 | 3 | 29.6 | 3.33 | ABCDEF |
| D | 1 to 3 | 5 | 34.53 | 0.57 | ABC |
| D | 1 to 4 | 3 | 34.77 | 0.5 | ABC |
| D | 2 to 1 | 5 | 31.69 | 0.88 | ABCDE |
| D | 3 to 1 | 5 | 30.49 | 0.19 | ABCDE |
| D | 4 to 1 | 4 | 28.36 | 1.2 | ABCDEFGH |
| L | 1 to 1 | 3 | 21.67 | 0.35 | DEFGHIJ |
| L | 1 to 2 | 3 | 21.2 | 0.32 | DEFGHIJ |
| L | 1 to 3 | 3 | 21.02 | 0.13 | EFGHIJ |
| L | 1 to 4 | 3 | 20.43 | 0.13 | DEFGHIJ |
| L | 2 to 1 | 3 | 23.93 | 0.32 | CDEFGHIJ |
| L | 3 to 1 | 3 | 24.4 | 0.09 | CDEFGHIJ |
| L | 4 to 1 | 3 | 24.81 | 0.08 | CDEFGHIJ |
| R | 1 to 1 | 3 | 14.06 | 3.81 | J |
| R | 1 to 2 | 3 | 16.82 | 5.23 | HIJ |
| R | 1 to 3 | 3 | 31.13 | 1 | ABCDE |
| R | 1 to 4 | 3 | 31.96 | 1.16 | ABCD |
| R | 2 to 1 | 5 | 20.24 | 1.22 | EFGHIJ |
| R | 3 to 1 | 3 | 20.71 | 2.76 | DEFGHIJ |
| R | 4 to 1 | 6 | 18.19 | 0.78 | FGHIJ |
| ST | 1 to 1 | 3 | 16.91 | 4.74 | HIJ |
| ST | 1 to 2 | 3 | 26.21 | 3.17 | CDEFGHI |
| ST | 1 to 3 | 3 | 26.96 | 3.42 | BCDEFGHI |
| ST | 1 to 4 | 3 | 21.41 | 7.78 | DEFGHIJ |
| ST | 2 to 1 | 3 | 26.07 | 7.53 | CDEFGHI |
| ST | 3 to 1 | 3 | 24.07 | 6.17 | CDEFGHIJ |
| ST | 4 to 1 | 3 | 17.71 | 0.12 | GHIJ |
| T | 1 to 1 | 3 | 24.38 | 2.44 | CDEFGHIJ |
| T | 1 to 2 | 3 | 20.79 | 1.76 | DEFGHIJ |
| T | 1 to 3 | 3 | 27.75 | 1.92 | BCDEFGH |
| T | 1 to 4 | 3 | 15.83 | 3.12 | IJ |
| T | 2 to 1 | 3 | 28.52 | 9.7 | ABCDEFG |
| T | 3 to 1 | 3 | 18.46 | 3.52 | FGHIJ |
| T | 4 to 1 | 3 | 27.96 | 2.47 | BCDEFGH |

For delta E with a blue-green control (testing how different the blend values are from the carrying capacity color of each oil with the blue-green pigment), the two-way ANOVA was significant at P<0.0001. The most difference was in refined linseed oil at the 1 to 4 green to red blend (34.08), although that combination was not significantly different from refined linseed oil 1 to 3 (33.20), tung oil at 4 to 1 (30.91), 1 to 3 (30.87), 2 to 1 (28.57), 1 to 1 (27.98), sun-thickened linseed oil at 1 to 3 (27.22), 1 to 2 (25.61), 2 to 1 (23.89), 3 to 1 (21.59), and Danish oil at 1 to 3 (26.95) and 1 to 4 (26.90).

When using red as the control, the two-way ANOVA was significant at P=0.05. Very few of the blends in this group differed significantly. The most change was seen in sun-thickened linseed oil at the 2 to 1 blend (47.96), and the least was in Danish oil at the 1 to 3 blend (5.57). These amounts were significantly different from one another, but not from many other values.

Blue red yellow blend. When using oil only as the control, the one-way ANOVA was significant at P=0.03. Danish oil had the highest difference (31.41) and refined linseed oil had the lowest (21.52). These two oils were significantly different from one another, but not from the other oils tested.

When blue-green pigment was used as the control, the ANOVA was significant at P=0.0002. Sun-thickened linseed oil had the highest difference (30.11) but was only significantly different from the lowest difference, raw linseed oil (8.854). For the red control the ANOVA was significant at P=0.0028. Sun-thickened linseed oil was again the highest (48.29), although it was not significantly different from raw linseed oil (21.21). The lowest difference was with cold-pressed linseed oil (7.52), which did not differ from the remaining oils tested. The ANOVA for the yellow control was significant at P=0.0089. Sun-thickened linseed oil had the most difference (30.30) but was only significantly different from the lowest difference, refined linseed oil (13.73).

For the red control, the ANOVA was significant at P=0.0028. Sun-thickened linseed oil had the highest delta E (48.29), which did not differ significantly from raw linseed oil (21.20). Raw linseed oil did not differ significantly from any other oil. For the yellow control, sun-thickened was again the highest delta E (30.30), and did not differ from raw linseed (25.86), cold-pressed (24.34), or Danish (21.70). The ANOVA was significant at P=0.0089.

Blue yellow blend. With the base oil as the control, the two-way ANOVA was significant at P=0.04, with an interaction between oil and distribution. The highest delta E values came from cp_4_1 and cp_3_1, but were not significantly different from many others (see Table 3). The only oil that had a significantly different delta E value between distributions was sun thickened linseed oil, where the one to three and one to four distributions had a significantly lower delta E than the two to one distribution.

TABLE 3

Delta E values and significant differences for blends of blue-green and yellow pigments in oils. Control values use base oil color. CP = cold-pressed oil, D = Danish oil, L = raw linseed oil, R = refined linseed oil, ST = sun-thickened linseed oil, T = tung oil, W = walnut oil. Different letters indicate significant differences at alpha = 0.05.

| Oil | Distribution | N | Mean | SD | Significant Difference |
|---|---|---|---|---|---|
| CP | 1 to 1 | 3 | 30.61 | 12.84 | ABC |
| CP | 1 to 2 | 3 | 31.4 | 15.9 | AB |
| CP | 1 to 3 | 3 | 27.17 | 15.16 | ABCDE |
| CP | 1 to 4 | 3 | 26.78 | 14.43 | ABCDE |
| CP | 2 to 1 | 3 | 21.05 | 1.3 | ABCDEF |
| CP | 3 to 1 | 3 | 34.44 | 12.11 | A |

TABLE 3-continued

Delta E values and significant differences for blends of blue-green and yellow pigments in oils. Control values use base oil color. CP = cold-pressed oil, D = Danish oil, L = raw linseed oil, R = refined linseed oil, ST = sun-thickened linseed oil, T = tung oil, W = walnut oil. Different letters indicate significant differences at alpha = 0.05.

| Oil | Distribution | N | Mean | SD | Significant Difference |
|---|---|---|---|---|---|
| CP | 4 to 1 | 3 | 35.18 | 11.54 | A |
| D | 1 to 1 | 3 | 25.2 | 9.02 | ABCDEF |
| D | 1 to 2 | 4 | 14.55 | 2.27 | ABCDEF |
| D | 1 to 3 | 4 | 23.68 | 7.69 | ABCDEF |
| D | 1 to 4 | 3 | 8.78 | 1.91 | DEF |
| D | 2 to 1 | 3 | 17.37 | 1.79 | ABCDEF |
| D | 3 to 1 | 3 | 15.71 | 2.55 | ABCDEF |
| D | 4 to 1 | 3 | 26.28 | 6.52 | ABCDE |
| L | 1 to 1 | 3 | 22.07 | 0.16 | ABCDEF |
| L | 1 to 2 | 3 | 22.24 | 0.2 | ABCDEF |
| L | 1 to 3 | 3 | 21.55 | 0.14 | ABCDEF |
| L | 1 to 4 | 3 | 21.16 | 0.06 | ABCDEF |
| L | 2 to 1 | 3 | 23.53 | 0.07 | ABCDEF |
| L | 3 to 1 | 3 | 23.9 | 0.05 | ABCDEF |
| L | 4 to 1 | 3 | 24.01 | 0.15 | ABCDEF |
| R | 1 to 1 | 3 | 9.65 | 0.51 | CDEF |
| R | 1 to 2 | 3 | 10.94 | 2.77 | BCDEF |
| R | 1 to 3 | 3 | 9.02 | 0.81 | CDEF |
| R | 1 to 4 | 3 | 6.23 | 1.53 | EF |
| R | 2 to 1 | 3 | 10.63 | 0.09 | BCDEF |
| R | 3 to 1 | 3 | 13.7 | 2.4 | ABCDEF |
| R | 4 to 1 | 3 | 7.16 | 0.17 | DEF |
| ST | 1 to 1 | 3 | 12.48 | 4.53 | BCDEF |
| ST | 1 to 2 | 3 | 7.98 | 2.91 | DEF |
| ST | 1 to 3 | 3 | 5.69 | 0.56 | EF |
| ST | 1 to 4 | 3 | 4.62 | 0.74 | F |
| ST | 2 to 1 | 3 | 28.31 | 13.7 | ABCD |
| ST | 3 to 1 | 3 | 12.31 | 1.31 | BCDEF |
| ST | 4 to 1 | 3 | 14.83 | 1.25 | ABCDEF |

When the blue-green pigment was used as the control, the 2-way ANOVA was significant, with the interaction between oil and distribution significant at P=0.0009. The Tukey HSD showed cold-pressed linseed oil at the one to four distribution to have the highest delta E value (29.66), however this amount was not statistically different from any of the other cold-pressed distributions, nor many of the other oils and distributions as well. When yellow was used for the control, the ANOVA was again significant, with the oil and distribution interaction significant at P=0.03. Once again, the cold-pressed linseed oil showed the highest delta E. The two highest values came from cold-pressed at the four to one concentration (31.30) and cold pressed at the three to one concentration (30.72), and the two did not differ significantly from one another or any other oil/concentration except sun-thickened linseed oil at the one to three concentration (4.06) and sun-thickened linseed oil at the four to one concentration (3.22).

Red yellow blend. The two-way ANOVA for the base oil color control was significant at P<0.0001. There was a significant interaction between oil and distribution at P<0.0001. The highest delta E came from cold-pressed linseed oil at the two to one distribution (33.96) and the Danish oil three to one distribution (33.82). These two did not differ significantly from many others, and there were no differences between the distributions in the Danish or cold-pressed linseed oil values.

When the red pigment was used as the control, there were no significant differences between any pigment or oil. For the yellow, the ANOVA was significant at P<0.0001, and there was a significant interaction between oil and distribution at P=0.0007. Tukey HSD showed the raw linseed oil at the four to one concentration to have the highest delta E (34.54), although it was not different from any other linseed distribution. It did differ from all the walnut oil distributions.

In view of the many possible embodiments to which the principles of the disclosed invention may be applied, it should be recognized that the illustrated embodiments are only preferred examples of the invention and should not be taken as limiting the scope of the invention.

What is claimed is:

1. A composition comprising a fungal pigment suspended or solvated in an oil carrier, wherein the fungal pigment is an extracellular pigment from a fungi selected from the *Chlorociboria* genus, the *Scytalidium* genus, or any mixture thereof, and wherein the composition does not include an organic solvent.

2. The composition of claim 1, wherein the oil carrier is a plant oil, mineral oil or animal oil.

3. The composition of claim 1, wherein the oil carrier is a vegetable oil.

4. The composition of claim 1, wherein the oil carrier is selected from sunflower, olive, walnut, tung, linseed, Danish oil, or a mixture thereof.

5. The composition of claim 1, wherein the composition is a liquid.

6. A wood finish composition comprising the composition of claim 1.

7. A paint composition comprising the composition of claim 1.

8. A method for staining an object, comprising applying to the object the composition of claim 1.

9. The method of claim 8, wherein the object comprises wood.

10. A method for dyeing an object, comprising applying to the object the composition of claim 1.

11. The method of claim 10, wherein the object comprises wood.

12. A method for painting an object, comprising applying to the object the composition of claim 1.

13. The method of claim 12, wherein the object comprises wood.

14. The composition of claim 1, wherein the oil carrier is raw linseed oil.

15. The composition of claim 1, wherein the fungal pigment is from a fungi selected from *C. aeruginascens, C. aeruginosa, S. cuboideum, S. lignicola, S. ganodermophthorum*, or a mixture thereof.

16. The composition of claim 15, wherein the oil carrier is raw linseed oil.

17. The composition of claim 15, wherein the oil carrier is selected from sunflower, olive, walnut, tung, linseed, Danish oil, or a mixture thereof.

18. The composition of claim 1, wherein the fungal pigment is water insoluble.

19. A method for resolubilizing a fungal pigment, comprising contacting a fungal pigment with the composition of claim 1 to provide a composition comprising the fungal pigment suspended or solvated in the oil carrier.

20. The method of claim 19, wherein the object comprises wood.

21. A method for making a composition comprising:

preparing a fungal pigment/organic solvent solution or suspension;

mixing the fungal pigment/organic solvent solution or suspension with an oil carrier; and evaporating the organic solvent resulting in a composition comprising the fungal pigment suspended or solvated in the oil carrier, wherein the fungal pigment is an extracellular pigment from a fungi selected from the *Chlorociboria* genus, the *Scytalidium* genus, or any mixture thereof, and wherein the composition does not include an organic solvent.

22. The method of claim 21, wherein the oil carrier is a plant oil, mineral oil or animal oil.

23. The method of claim 21, wherein the oil carrier is raw linseed oil.

24. The method of claim 21, wherein the fungal pigment is from a fungi selected from *C. aeruginascens, C. aeruginosa, S. cuboideum, S. lignicola, S. ganodermophthorum*, or a mixture thereof.

25. The method of claim 21, wherein preparing a fungal pigment/organic solvent solution or suspension comprises extracting the fungal pigment from wood with the organic solvent.

26. The method of claim 25, wherein the organic solvent is selected from dichloromethane, chloroform, pyridine, acetone, tetrahydrofuran, or acetonitrile.

27. The method of claim 25, wherein the organic solvent is selected from dichloromethane, chloroform, or pyridine.

28. A method for making a composition comprising:

preparing a fungal pigment/organic solvent solution or suspension;

mixing the fungal pigment/organic solvent solution or suspension with a water carrier; and removing the organic solvent resulting in a composition comprising the fungal pigment suspended or solvated in the water carrier, wherein the fungal pigment is an extracellular pigment from a fungi selected from the *Chlorociboria* genus, the *Scytalidium* genus, or any mixture thereof, and wherein the composition does not include an organic solvent.

* * * * *